(12) United States Patent
Sutherland et al.

(10) Patent No.: US 10,987,155 B2
(45) Date of Patent: Apr. 27, 2021

(54) BIPOLAR FORCEPS WITH FORCE MEASUREMENT

(71) Applicants: Garnette Roy Sutherland, Calgary (CA); Kourosh Zareinia, Calgary (CA); Liu Shi Gan, Calgary (CA); Tomas Jens Hirmer, Calgary (CA); Sanju Lama, Calgary (CA)

(72) Inventors: Garnette Roy Sutherland, Calgary (CA); Kourosh Zareinia, Calgary (CA); Liu Shi Gan, Calgary (CA); Tomas Jens Hirmer, Calgary (CA); Sanju Lama, Calgary (CA)

(73) Assignee: OrbSurgical Ltd.

( * ) Notice: Subject to any disclaimer, the term of this patent is extended or adjusted under 35 U.S.C. 154(b) by 0 days.

(21) Appl. No.: 13/930,361

(22) Filed: Jun. 28, 2013

(65) Prior Publication Data

US 2015/0005768 A1    Jan. 1, 2015

(51) Int. Cl.
*A61B 18/14* (2006.01)
*A61B 18/00* (2006.01)
*A61B 90/00* (2016.01)

(52) U.S. Cl.
CPC ............ *A61B 18/1442* (2013.01); *A61B 2018/00791* (2013.01); *A61B 2018/00898* (2013.01); *A61B 2018/1462* (2013.01); *A61B 2090/065* (2016.02); *A61B 2218/002* (2013.01)

(58) Field of Classification Search
CPC .......... A61B 17/28; A61B 17/282; A61B 2017/2932; A61B 2017/445; A61B 18/1442; A61B 18/1445; A61B 2018/00297; A61B 2018/00303; A61B 2018/00309; A61B 2018/00898; A61B 2018/00773; A61B 2019/2292; A61B 2019/464; A61B 2019/465
USPC .................................................. 606/51–52
See application file for complete search history.

(56) References Cited

U.S. PATENT DOCUMENTS

| | | | |
|---|---|---|---|
| 5,637,110 A * | 6/1997 | Pennybacker et al. ......... 606/46 |
| 5,720,742 A * | 2/1998 | Zacharias .......................... 606/1 |
| 8,298,227 B2 * | 10/2012 | Leo et al. ........................ 606/41 |
| 8,603,084 B2 * | 12/2013 | Fish et al. ....................... 606/34 |
| 2010/0286691 A1 * | 11/2010 | Kerr et al. ....................... 606/51 |
| 2011/0087112 A1 * | 4/2011 | Leo et al. ...................... 600/478 |
| 2012/0123404 A1 * | 5/2012 | Craig ............................... 606/33 |
| 2012/0172873 A1 * | 7/2012 | Artale ................. A61B 18/1442 606/46 |

(Continued)

*Primary Examiner* — Ronald Hupczey, Jr.
(74) *Attorney, Agent, or Firm* — Miller Thomson LLP; David J. Schnurr

(57) ABSTRACT

Bipolar forceps of the type where each of the prongs has a manually engageable portion spaced from the tip for manual squeezing of the prongs and an electrical supply system for applying a high-frequency electric current between tool tips to dissect through tissue planes and/or seal blood vessels includes a set of force measuring sensors for measuring forces, particularly squeezing forces, applied to the prongs at the tip. A temperature sensor is included to provide temperature information and temperature compensation. The sensors are applied to each prong in opposing pairs on the inside and outside surfaces and the outputs thereof are applied to a bridge arrangement. The signals are sent to a processor for generating warning signals and for recording forces for training purposes where a haptic system can be used.

16 Claims, 4 Drawing Sheets

(56) References Cited

U.S. PATENT DOCUMENTS

2014/0025067 A1\* 1/2014 Kerr .................. A61B 18/1445
606/41

\* cited by examiner

BIPOLAR FORCEPS WITH FORCE MEASUREMENT

This invention relates to a bipolar forceps construction for use in dissecting or electro-cauterization of tissue in surgical procedures.

BACKGROUND OF THE INVENTION

The arrangement described herein focuses on human interaction with technology within the field of medicine. The arrangement described herein provides a force-sensing dissecting bipolar forceps tool. The application and translation areas for this tool include conventional and robotic surgery, surgical training, and surgical simulation. A dissecting bipolar forceps is an electro-cauterization forceps used worldwide in operating rooms and utilizes high-frequency electric current between tool tips to dissect through tissue planes or seal blood vessels. A dissecting bipolar forceps with the ability to also measure the forces of dissection has not been made available to the neurosurgical community to date.

The bipolar forceps is one of the primary tools used in neurosurgery. There are more than 2400 hospitals in the USA and Canada equipped with neurosurgical operating rooms. There are multiple neurosurgeries per day in each of these hospitals. Neurosurgeons typically have multiple bipolar forceps of varying length and shape on hand for use during each surgical case. Therefore, in neurosurgery alone, there is a strong demand for bipolar forceps tools. Furthermore, considering disposable bipolar forceps increases the demand drastically. It should also be noted that bipolar forceps are used in other surgical disciplines as well.

In general such tools comprise a pair of prongs each having a prong tip where the prongs are connected for relative movement of the prongs for movement of the tips into a tip contacting position and each of the prongs has a manually engageable portion spaced from the tip for manual movement of the prongs to the tip contacting position by manual pressure on the manually engageable portion. An electrical supply system connected to an end of the prongs remote from the tip is provided for applying a high-frequency electric current between tool tips to dissect through tissue planes and/or seal blood vessels.

SUMMARY OF THE INVENTION

According to one aspect of the invention there is provided a bipolar forceps tool comprising:

a pair of prongs each having a prong tip;

the prongs being connected for relative movement of the prongs for movement of the tips into a tip contacting position;

each of the prongs having a manually engageable portion spaced from the tip for manual movement of the prongs to the tip contacting position by manual pressure on the manually engageable portion;

an electrical supply system for applying a high-frequency electric current between tool tips to dissect through tissue planes and/or seal blood vessels;

and at least one force sensing component for measuring forces applied to the prongs at the tip.

The force sensing component can be arranged for measuring forces applied to the prongs by contact pressure between the tips at the tip contacting position, for measuring forces applied to the prongs laterally of the tip by pulling the tip transversely of the prongs and/or by pulling the tip longitudinally of the prongs.

Preferably both of the prongs have force sensing components thereon where the forces in both prongs are detected in a composite or independent manner.

Preferably there is provided a temperature sensing component on at least one of the prongs for measuring temperatures of tissue dissection and coagulation in surgical procedures.

Preferably the force sensing and temperature sensing components are protected by a protective coating/covering on the prongs in such a way as to support standard medical sterilization procedures on the forceps.

Preferably the means for measuring includes for each prong four sensing components, the outputs of which are connected in a full-bridge electrical circuit configuration.

Preferably there is provided for the force sensing components an arrangement for compensating for temperature fluctuations during force measurement. This can be an arrangement for temperature compensation comprises a temperature reference force sensing component located at a position so as to be at a common temperature with the force sensing component and arranged so as to be non-responsive to the forces so as to provide a temperature compensation signal where for example the temperature reference force sensing component is mounted perpendicularly to the force sensing component.

Preferably there is provided a display for displaying the forces and temperatures of tissue dissection and coagulation in surgical procedures present in both prongs of the bipolar forceps in a composite or independent manner.

Preferably the display includes embedded electronic displays, smart phones, tablets, computers, or augmented/virtual reality eye-glasses.

Preferably there is provided a force warning system that indicates to the user when force thresholds are being exceeded via visual, audio and haptic means.

Preferably there is provided a temperature warning system that indicates to the user when temperature thresholds are being exceeded via visual, audio and haptic means.

Preferably there is provided an irrigation system for supplying irrigating fluid to the tips, where an amount of irrigation is delivered when a temperature threshold is exceeded.

Preferably there is provided a computer control system which operates for translating accurate forces of dissection, based on force recordings from real surgeries, into simulation software creates a training platform for novice surgeons with increased realism for tool-tissue interaction.

Preferably there is provided as part of the system haptic force-generating forceps for operation in the training platform.

Preferably there is provided a computer control system which operates for collecting data from clinical studies to be made available for incorporation into surgical simulation software.

Preferably there is provided a force calibration device customized for surgical forceps to allow strain sensor voltages to be mapped to actual forceps-tip forces.

Preferably there is provided a computer control system which operates to collect data at precise timing to reflect the changes in forces while the tool is being used on different tissue types.

The arrangement described herein provides addition of force sensors to bipolar forceps which allows the quantification of dissection forces during neurosurgery.

The arrangement described herein can provide one or more of the following features:
- force and temperature warning and data recording in a bipolar forceps dissection and cauterization tool, while preserving standard functionality and allowing tool sterilization.
- is the first "smart/intelligent" bipolar forceps tool;
- includes force and temperature warning systems, as well as a temperature-triggered self-irrigation feature.
- Also integrates display technologies and different warning modalities (e.g. haptics, audio, visual).

Thus, the arrangement described herein incorporates force sensors into the dissecting bipolar forceps in order to measure and record accurate forces of tissue dissection. The arrangement described herein advances the safety and performance of conventional surgery, and incorporating the arrangement described herein into robotics increases surgeons' confidence in the tools used to perform robot-assisted surgeries. Furthermore, translating accurate forces of dissection, based on force recordings from real surgeries, into simulation software creates a training platform for novice surgeons with increased realism for tool-tissue interaction.

The following problems are required to be considered:
- the mounting of the force sensors is necessary without interfering with the standard functionality of the bipolar forceps tool.

It is required to cover the sensors and wires and to coat the tool prongs to allow for tool sterilization.

It is necessary to provide the optimal number of force sensors and their optimal configuration (mechanically and electrically). Typically the arrangement described herein uses four force sensors per prong. This is because a full-bridge electrical configuration is used for the sensor interconnections, since it is one of the more sensitive configurations and also exhibits a linear response (while other configurations do not). Both half-bridge and full-bridge configurations grant greater sensitivity over the quarter-bridge circuit, but often it is not possible to bond complementary pairs of sensors to the test specimen.

The arrangement described herein creates a digital interface with a high-force warning safety system for bipolar forceps where none previously existed. Building additional safety features into surgical procedures is highly desirable for both surgeons and patients. This significantly augments a surgeon's ability to assess force exertion during delicate surgical procedures. The arrangement described herein produces an innovative tool that has implications for surgical safety, performance, and training. There is an increasing demand for this type of digital surgical interface, particularly as surgical education requires effective solutions to resource-intensive training. Furthermore, the pairing of a force-sensing forceps (equipped with force recording capabilities) with a haptic force-generating forceps already developed to mirror surgeon's tool forces to a trainee is a unique training approach. This additional sensory feedback allows surgical trainees to experience the actual tool-tissue interaction forces and tool movements of an experienced surgeon, while watching and listening to an operation. This results in a surgical education environment that incorporates haptic (touch) feedback in addition to traditional visual and audio sensory modalities.

The arrangement described herein provides a microsurgical force-sensing bipolar forceps tool for measuring the forces of dissection in neurosurgery. The arrangement described herein is equipped with a force warning safety system (e.g. with visual, audio, and haptic alerts). The arrangement described herein, customized specifically for the requirements of neurosurgery, allows tool-tissue interaction forces to be studied and more rigorously quantified. Testing will determine the forces of dissection for various neurological tissues and different surgical procedures on human brains. This data will then be used to calibrate force thresholds for the warning safety system.

The data from clinical studies will be made available for incorporation into surgical simulation software. Simulation models are currently based on estimated forces, and therefore estimated tissue deformation. The force data can be used in conjunction with different brain tissue models to create more realistic tool-tissue interaction. In existing simulation software, mass-spring models and finite element methods are typically used. With the ability to more accurately record forces over time, improved modeling coefficient estimates (e.g. damping coefficients, material constants, etc.) will be generated. These simulation models will greatly enhance the capability to provide surgeons with realistic case rehearsal and training. In order for surgical simulators to be an effective preparation for real surgical procedures, realistic feedback on the trainee's interactions with the virtual tissues is required. The more realistically the tool-tissue forces are simulated, the more effective the simulator will be in preparing the trainee for performance in the operating room (OR). Similar to the force warning safety system, the virtual surgical simulation environment can also benefit from an analogous feature. This improvement can only be implemented if a safe range of realistic dissection forces for specific tissues is known. In the safety of a virtual simulation environment, tool force warning indicators would help surgical trainees to practice avoiding tissue damage during dissections. Before entering the OR, surgical trainees can practice on realistic surgical simulators and compare their simulation performance to the performance of experienced surgeons during real surgeries (where force data was collected). Video and tool-tip-forces can be recorded simultaneously, allowing the procedure to be replayed providing both video and haptic feedback (using the Haptic Forceps). This is one means of case rehearsal where a surgeon or trainee can feel the surgical forces as they watch procedures.

The arrangement described herein can easily be paired with a surgical navigation system. This allows the tool to be registered in 3-D space, enabling the determination of position coordinates. Customized software can then monitor the tip position with respect to critical anatomical structures during a surgery. If the tip moves within a configurable threshold of a critical anatomical structure, the warning system is activated. In order to determine which critical anatomical zones to avoid, the software uses the pre-operative imaging data in conjunction with the navigation system and the surgeon's pre-operative input based on anatomical knowledge.

The arrangement described herein assists the ongoing development of robotic tools. Presently tool-tip forces on a surgical robot are calculated using the force sensor measurements at the end-effector of a robotic manipulator. These calculations are based on the kinematics and dynamics of the robotic manipulator, tool holder, and the surgical tool. Approximations are involved in these calculations, which introduce small force inaccuracies. Measuring forces directly at the tool tip in the arrangement described herein provide greater accuracy.

In any type of sensor, resolution and accuracy are the most important characteristics. The resolution of a sensor is the smallest change in the quantity of measurement detectable by the sensor. Two different types of sensors can be used in the arrangement described herein.

The first approach relies on optical fiber Bragg grating (FBG) strain sensors.

The second approach focuses on conventional strain gauges.

Each of these technologies has advantages and disadvantages.

The advantages of optical sensors include high sensitivity, small size, fast response time, complete electrical isolation from other electronics, and MRI compatibility. This last characteristic is essential for use with MRI compatible robots. However, optical force sensors are much more expensive than conventional strain gauges (at least 20 times more). The optical-based sensor has superior precision and is MRI compatible, allowing it to be used inside the bore of an MRI magnet. The arrangement described herein can also use conventional strain gauges which are cost effective and therefore more likely will be used for surgical training. Moreover, the low cost of the strain gauge forceps make them suitable to be provided in disposable surgical tools.

The arrangement described herein using optical technology is highly sensitive with a resolution of less than 1 millinewton.

Strain gauges are the most commonly used technology in force and pressure sensors. A strain gauge is a device used to measure the strain, or deformation, of an object. A strain gauge is usually a flexible foil pattern that consists of several thin conductive parallel wires sandwiched between two layers of supporting material. It forms a resistive elastic unit, in which a change in resistance is a function of applied strain. Measuring forces using strain gauges is a well-established technology. Conventional strain gauges have been selected as an option in this proposal because of their ease of use, low cost, and established reputation.

The principle of a strain gauge is based on changes in the resistance of a wire correlated to increases and decreases in strain. When the strain gauge is properly attached to the surface of an object, strain to the object causes the two to deform together. This in turn changes the resistance of the strain gauge. To convert the change in resistance to strain, the sensitivity factor of the strain gauge material must first be determined. The sensitivity factor is different for different strain gauge materials. Thus, choosing a proper strain gauge according to the specific application is important. There are also other design factors that should be considered to minimize error, such as variation due to temperature, linearity, hysteresis, overloading, humidity, and repeatability.

One major issue is temperature compensation as bipolar forceps produce heat during coagulation of tissue. One way of resolving this temperature issue, involves installing two strain gauges at each force-sensing site on the forceps prongs. One strain gauge will serve as a strain sensor, and the second will act as temperature reference, to compensate for errors caused by fluctuations in temperature. These coupled strain gauges are mounted close enough to have the same temperature; however one of them is isolated from strain. One way to achieve this is by having the temperature reference strain gauge mounted perpendicularly to the strain-sensing one.

The simplest design is to have one strain sensor installed on each forceps prong. To achieve higher resolution, four strain sensors are required (two on each prong). Compensating for the effects of temperature variations requires attaching eight strain sensors (four on each prong).

The strain sensors can be arranged in different configurations on the forceps for measuring deformation with the greatest precision. Strain sensors arranged for measuring the forces transverse to the prong of the forceps, that is in the direction of compression between the tips of the prongs or the squeezing/dissecting forces (x-axis) can be placed on the inside and outside of the forceps prongs to achieve better precision. The best strain sensor placement is where the greatest deformation occurs on the prong of the tool, which varies between different types of forceps. The arrangement described below shows the sensor arrangement with the sensors on the inner and outer side faces of the prongs for measuring the squeezing/dissecting forces (x-axis). Theoretically, the arrangement could also measure forces in the y-axis using the same concept with the sensors mounted on the top and bottom faces of the forceps prongs. Measurement in the longitudinal direction of the prongs is also possible but the forceps would need to be physically modified to measure forces on the z-axis, potentially affecting tool functionality. The precise sensor placement depends on specific forceps geometry. Placement of the sensors is located at the position of maximum deformation of the prongs during compression or squeezing and therefore maximum strain. The configuration of the sensors is arranged in adjacent opposing pairs.

Since strain sensor readings are based on material deformation, material choices are highly relevant to forceps selection. As dissecting bipolar forceps already have an attached cable, the geometry of the tool is not changed with the addition of sensors and their wires. The ergonomics of the tool remains identical to that of conventional bipolar forceps, while adding accurate force measurement functionality.

A force calibration device customized for surgical forceps is provided to allow strain sensor voltages to be mapped to actual forceps-tip forces. This calibration device has a titanium Nano17 accurate force sensor installed in it (ATI Six-Axis Force/Torque sensor). The Nano17 titanium force sensor was chosen for its superior resolution and accuracy. The titanium version of this force sensor has the benefit of being MR-safe. These sensors can be calibrated with different standards to achieve various resolutions. For the arrangement described herein, the force sensor will use the SI-8-0.05 standard, since it provides the highest resolution (1/682N).

The arrangement described herein includes a display system with integrated high-force warning safety feature (human interaction with digital information).

The arrangement described herein includes a display system component that allows the end-user (surgeon) to observe the instantaneous force readings at the tips of the tool. Surgeons may have different display system preferences and by designing a modular system for displaying the force readings, the arrangement described herein provide a flexible and customizable solution to the end-user. The display system also provides optional audio alerts. Furthermore, both wireless and wired implementations can be provided for communication between the tool and the display system. The display system options include:

Wristband display system: force readings are displayed on a wristband worn by the surgeon.

Eyeglasses display system: force readings are displayed non-obtrusively on a pair of eyeglasses worn by the surgeon (similar to the Google Glass Project).

Tablet/Smart Phone system: force readings are displayed on a mobile device. This facilitates remote monitoring of a surgery for training purposes.

The knowledge of average dissection forces and maximum force limits for different tissues is essential in the development of warning indicators for tissue dissection during surgery. One significant feature of the arrangement described herein is to provide a high-force warning safety system for use with force-sensing bipolar forceps. The force data collected from the pre-clinical and clinical trials indicates safe force ranges for different neurological tissue types during various surgical tasks. The tool can provide an audio, visual and/or haptic warning when approaching forces that could damage tissue. This warning system prevents surgeons from damaging tissue unnecessarily, increasing patient safety and improving outcome.

The tool (force-sensing) can be coupled with an existing set of forceps with haptic actuation (force-generating), which allows the forces applied by a surgeon during a surgery to be mirrored in the Haptic Forceps held by a surgical trainee. Currently, trainees observe surgeons at work, and use visual and audio feedback to anticipate the forces used for dissecting tissue. The addition of haptic feedback provides surgical trainees an effective means of feeling and understanding the forces applied during surgery, making the process of learning how to perform surgery more efficient.

The arrangement described herein can include a multi-platform content player application suite that allows modules of heterogeneous, platform-independent content to be written and deployed across various technology platforms including, but not limited to, iOS and Android mobile devices. The content modules can contain a mix of heterogeneous elements appropriate to a given operation or task such as dynamic simulations, plotting and analysis tools, hardware-in-the-loop interaction, 2D/3D visualization, audio cues, as well as multimedia to enhance the experience.

Since the forces exerted by the tool are small during microsurgical tasks, the data acquisition system needs to have precise timing to reflect the changes in forces while the tool is being used on different tissue types (e.g. dissection of cranial nerve vs. fibrous tissues).

The arrangement described herein can include master-slave setups, which consist of different haptic devices that act as master hand controllers, and a recently acquired industrial Kuka robot that acts as a slave. The original control system for the Kuka robot is customized to improve the control system sampling time, as well as to provide the ability to remotely control the robot over an ethernet network via different master hand controllers.

The long-term benefits of improving surgical simulation are widespread. Simulation allows trainees to learn and practice essential skills, from simple incisions to complex surgical scenarios, without the expense of practicing on a cadaver or the risk to a live patient. Surgeon training could become more cost-effective as a direct result of realistic simulation. Additionally, simulation allows case rehearsal, which will contribute to improved patient outcomes. Introducing new safety features based on tool-tissue interaction forces will provide tangible benefits to patients.

The tool is both user-friendly and effective, increasing the likelihood of achieving widespread adoption within the medical community. This technology addresses a current gap in the medical field by introducing a digital interface for measuring tool-tissue interaction forces.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
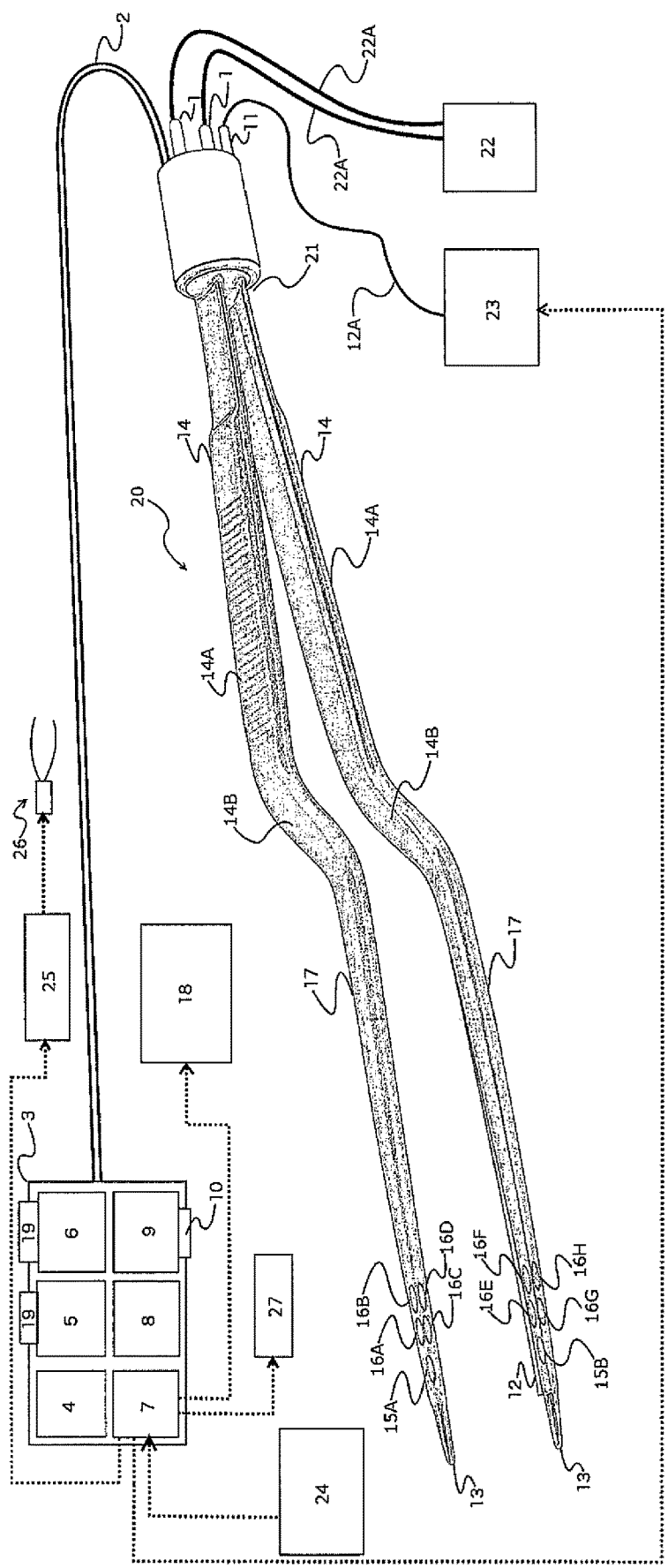
FIG. 1 is a schematic illustration of one embodiment of forceps according to the invention.

The figures include the following components:
1—Plugs for bipolar forceps tool power connection.
2—Wires that connect embedded computer 3 to sensors 15 & 16 mounted on the bipolar forceps tool.
3—Miniature embedded computer system.
4—Signal conditioner, amplifier and low pass filter module.
5—High-force warning system module.
6—High-temperature warning system module.
7—Wireless communications module.
8—Embedded display.
9—On-board data recording module.
10—Port for connecting on-board data recording module to external computer.
11—Irrigation port.
12—Irrigation tube.
13—Bipolar forceps tips are available in a range of different sizes.
14—Bipolar forceps prongs are available in a range of different lengths (shorter for surface procedures and longer for deeper surgical procedures).
15—Temperature sensors.
16—Force sensors or strain gauges.
17—Coating on bipolar forceps prongs to allow for sterilization.
18—Secondary wireless display (optional).
19—Haptic actuator interface ports.
20—bipolar forceps tool
21—handle
22—electrical supply system
23—irrigation actuation system
24—calibration device
25—system control computer
26—haptic force-generating forceps
27—data collection and transfer system The embodiment shown in FIG. 1 comprises a bipolar forceps tool 20 includes a pair of prongs 17 each having a prong tip 13 which are connected at the base or handle 21 for relative bending or squeezing movement of the prongs for movement of the tips 13 into a tip contacting position.

Each of the prongs has a manually engageable portion 14A spaced from the tip by a bend portion 14B for manual movement of the prongs to the tip contacting position by manual pressure on the manually engageable portion 14A.

An electrical supply system 22 is provided for applying a high-frequency (in the radio frequency range of approximately 100 kHz to 5 MHz) electric current between tool tips 13 to dissect through tissue planes and/or seal blood vessels.

Figure 2:
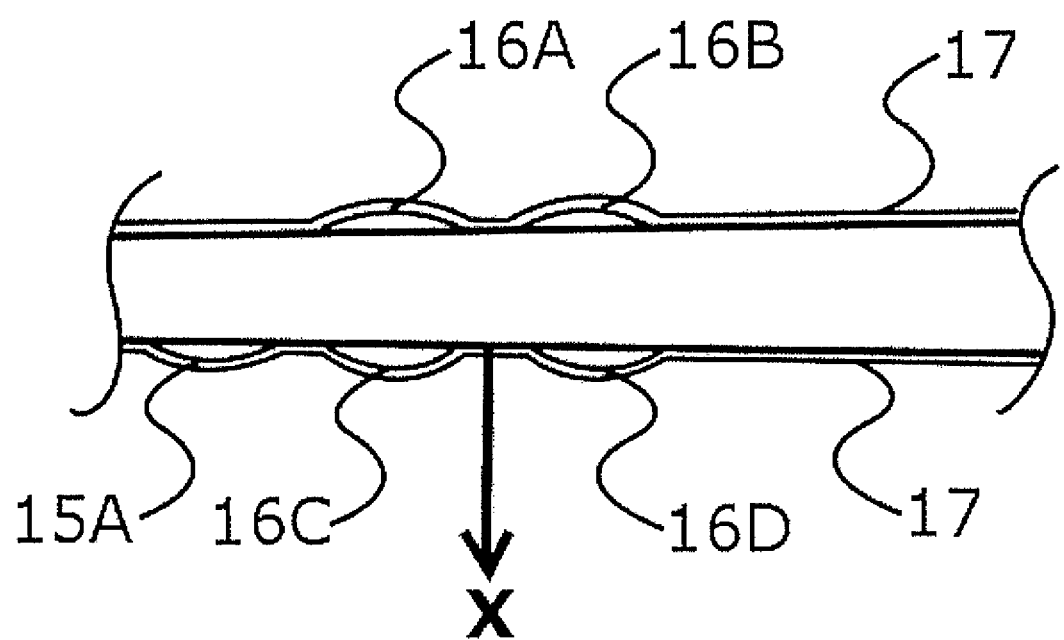
FIG. 2 is a view of the prongs only of the forceps showing the arrangement of four strain gauges installed on a dissecting bipolar forceps.

A series of force sensing components 16A to 16D and 16E to 16H are provided on each prong for measuring forces applied to the prongs at the tip. As shown in FIG. 2, these are arranged on the side faces of the rectangular cross-section of the prong which are at right angles to the X-axis in which the compression forces from squeezing the prongs together are measured. In the embodiment shown, no sensors are mounted on the top and bottom faces of the prongs since there is no measurement of forces in the Y-axis. However, in an alternative arrangement (not shown) additional sensors can be mounted on these faces.

The forces in both prongs are detected in a composite or independent manner in that the signals detected by the forces are transmitted through the output cable 2 consisting of a wire bundle having a plurality of individual communication wires to the computer for processing where they can be combined and analyzed for indication separately or as a combined force output signal.

One or both of the prongs also carries a temperature sensing component 15A, 15B for measuring temperatures of tissue dissection and coagulation in surgical procedures. This is located at or adjacent the tip so as to be closely responsive to the temperature of the surrounding tissue at the tip.

The force sensing and temperature sensing components 15, 16 are protected by a protective coating/covering 17 on the prongs in such a way as to support standard medical sterilization procedures on the forceps. This is particularly provided as discussed above in an arrangement using high cost sensors which require re-use.

The two types of sensors, strain gauges and optical force sensors, and can be physically mounted on the surfaces of the prongs in different manner to obtain the best connection. Preferably the mounting is by way of a special adhesive glue compound which ensures that the strain gauge follows the bending of the material forming the prong without distortion.

As shown in the configuration in FIG. 2, each prong carries four sensing components 16A to 16H. This includes an arrangement for compensating for temperature fluctuations during force measurement where the temperature sensing component 15A, 15B is located at a position immediately adjacent the sensors 16A to 16H respectively so as to be at a common temperature with the force sensing component and the temperature sensing device is arranged so as to be non-responsive to the forces by being arranged perpendicular to the force sensor so as to provide a temperature compensation signal.

That is the temperature sensor is installed in such a way so as to be isolated from strain to minimize strain on the temperature sensor as much as possible to provide a temperature compensation signal.

Figure 3:
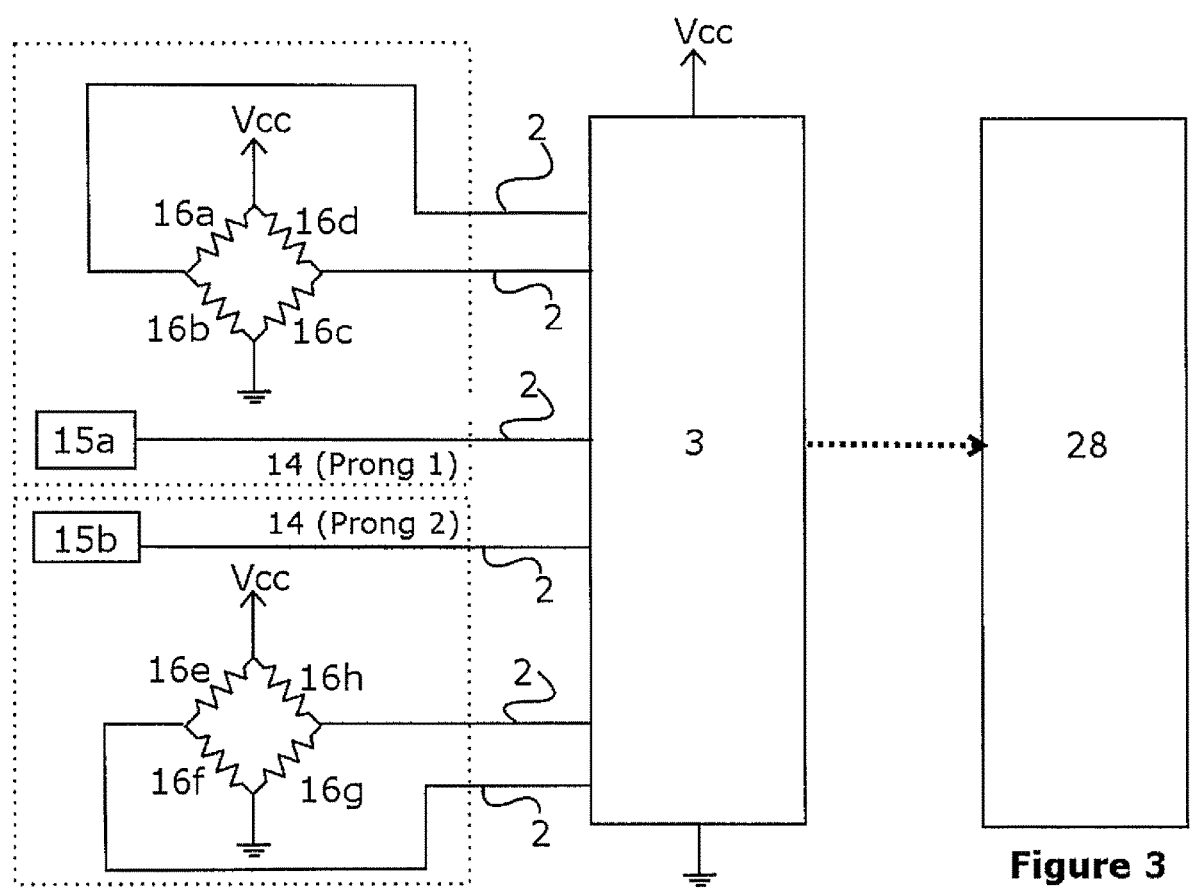
FIG. 3 shows the arrangement of the computer control of FIG. 1 including a bridge configuration connected to a signal-conditioning box that includes a low-pass filter and amplifier.
Figure 4:
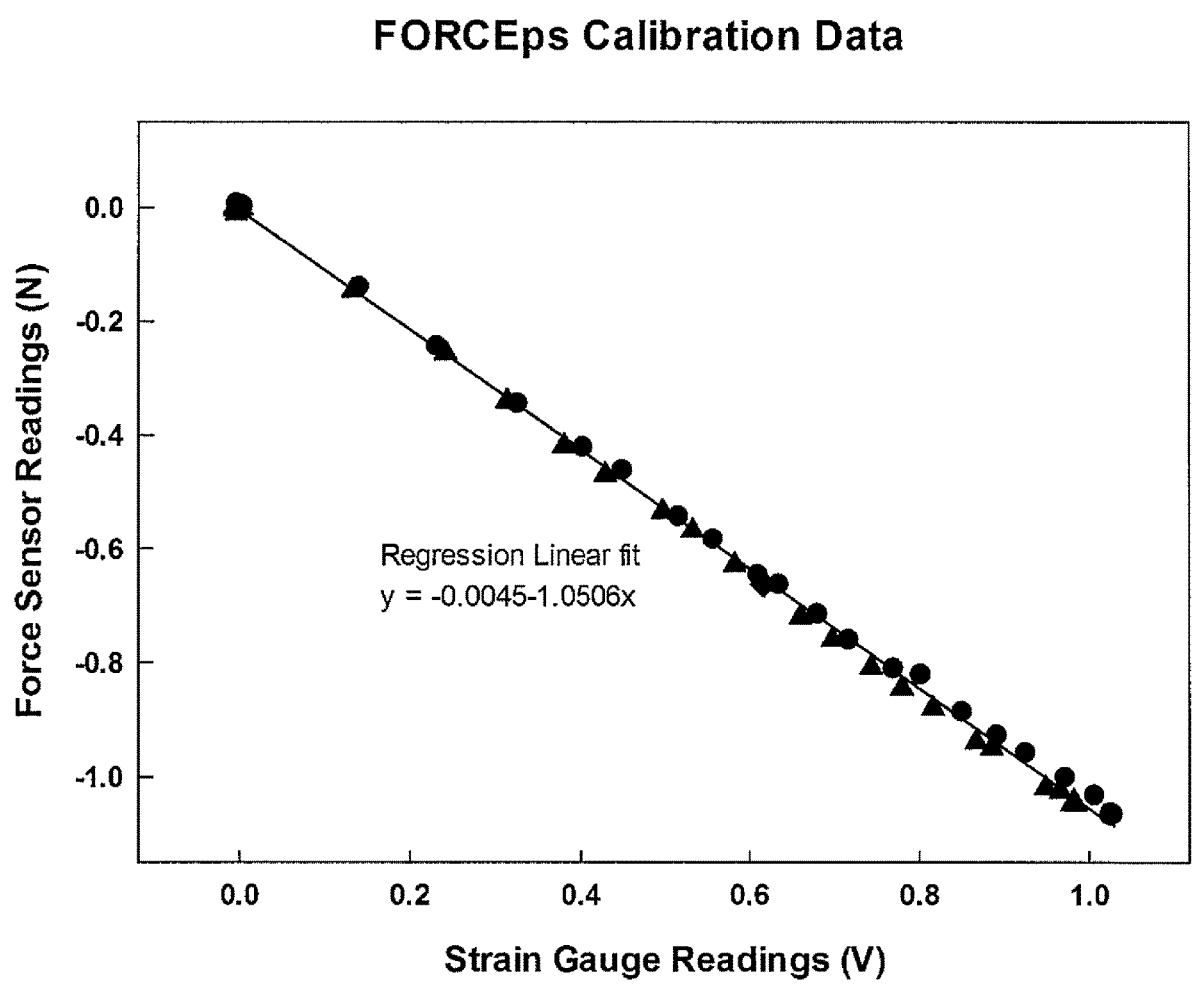
FIG. 4 is a graph showing a plot of force vs. voltage for calibration.

As shown in FIG. 3, the outputs of the force sensors 16A to 16D and 16E to 16H are connected in respective full-bridge electrical circuit configurations to the computer system 3 which manages the tool.

Also shown in FIG. 2 is the arrangement of the sensors 16A to 16D where two sensors 16A and 16B are one side face of the prong and the other sensors 16C and 16D are on the opposite side face. Also the sensor 16A is aligned directly opposite the sensor 16C and the sensor 16B is directly opposite the sensor 16D. This arrangement of sensors together with the full bridge arrangement of the connection of their electrical outputs has been found to provide a very effective analysis of the forces and a final output which is closely proportional to the squeezing force applied in the X-direction.

The computer system 3 includes a display 8 for displaying the forces and temperatures of tissue dissection and coagulation in surgical procedures present in both prongs of the bipolar forceps in a composite or independent manner. In addition the system includes a wireless communication module 7 for communication with an exterior display 18 which can include embedded electronic displays, smart phones, tablets, computers, or augmented/virtual reality eye-glasses.

The computer system 3 further includes a force warning system 5 that indicates to the user when force thresholds are being exceeded via visual, audio and haptic means.

The computer system 3 further includes a temperature warning system 6 that indicates to the user when temperature thresholds are being exceeded via visual, audio and haptic means.

The tool includes an irrigation system for supplying irrigating fluid though a duct 11 to be carried though channel (not shown) in one or both prongs to the tips, where an amount of irrigation is delivered when required either controlled by the surgeon in conventional manner or by the computer system 3 in the event that a temperature threshold is exceeded.

The computer system 3 includes a recording component 9 which operates for translating accurate forces of dissection, based on force recordings from real surgeries. The component 9 operates to collect data at precise timing to reflect the changes in forces while the tool is being used on different tissue types. This data can be transferred to a system control computer 25 which contains simulation software to create a training platform for novice surgeons with increased realism for tool-tissue interaction. The system of the computer 25 also includes haptic force-generating forceps 26 for operation in the training platform as used by training persons.

The wireless communication system 7 can also transfer data to a data collection and transfer system 27 for collecting data from clinical studies to be made available for incorporation into surgical simulation software.

There is also provided a force calibration device 24 customized for the surgical forceps 20 to allow strain sensor voltages actually detected by the sensors 16 to be mapped to actual forceps-tip forces from the calibration device 24.

Thus four strain gauges 16A to 16H are installed on a dissecting bipolar forceps. This bridge configuration is then connected to a signal-conditioning box 4 that includes a low-pass filter and amplifier. The output voltage of the signal-conditioning box 4 is connected to the analog input of a data acquisition board, which in turn is connected to a computer that reads and displays the voltages on a screen. A Nano17 force sensor is attached to a moving platform actuated by a motor and gearbox. The Nano17 force sensor is connected to its own signal conditioning box and data acquisition board (ATI and National Instruments). By pressing a push button, the motor is energized and the Nano17 force sensor moves towards the tool tip incrementally to increase the applied force at the tool tip. Forces (measured by Nano17) and voltages from the strain gauges are then used to obtain a force vs. voltage plot shown in FIG. 5.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A bipolar forceps tool comprising:
   a pair of prongs each prong having a shaft and a prong tip disposed distal to the shaft, the prong tip having a tissue contacting surface disposed thereon, the proximal end of each of the prongs terminating in a fixed connection point to a base;

the prongs being connected for relative movement of the prongs and associated movement of the tips;

an electrical supply system for applying an electric current between the tissue contacting surfaces of the prong tips;

an at least one strain sensor mounted on at least one of the prongs, the at least one strain sensor for measuring forces applied to the tissue contacting surfaces of the prongs;

wherein the at least one strain sensor is disposed between the tissue contacting surface and the fixed connection point; and wherein the at least one strain sensor is located at a position of maximum deformation of the at least one prong upon application of force to an outer surface of the at least one prong.

2. The bipolar forceps tool as claimed in claim 1 wherein the forces in both prongs can be detected in a composite or independent manner.

3. The bipolar forceps tool as claimed in claim 1 wherein said at least one strain sensor comprises two strain sensors arranged on opposite side faces of the prong, the outputs of which are connected in a full-bridge electrical circuit configuration.

4. The bipolar forceps tool as claimed in claim 1 wherein said at least one strain sensor comprises a strain gauge.

5. The bipolar forceps tool of claim 4 wherein there are three strain sensors each comprising a strain gauge, wherein the three strain sensors on each prong are positioned in three perpendicular planes to measure surgical forces along: (i) the axis perpendicular to the longitudinal axis of the prong and the tissue contacting surface of the prong tips, to measure compression and dissection forces; (ii) the axis perpendicular to the longitudinal axis of the prong and parallel to the tissue contacting surface of the prong tips, to measure upward and downward forces; and (iii) the longitudinal axis, to measure puncture forces; and wherein the combination of these three measured forces can be used to determine force vectors showing forces applied to the prong tips in any direction within a three-dimensional space.

6. The bipolar forceps tool of claim 4 wherein said at least one strain sensor detects a bending of the shaft and not pressure applied to the tissue contacting surfaces of the prong tips.

7. The bipolar forceps tools as claimed in claim 1 wherein said at least one strain sensor comprises an optical sensor.

8. The bipolar forceps tool as claimed in claim 1 further comprising a force calibration device arranged customized for surgical forceps to allow strain sensor voltages to be mapped to actual forces at the tips wherein the calibration device is used to determine a correlation between output signals from said strain sensors and the corresponding actual forces.

9. The bipolar forceps tool as claimed in claim 1 wherein the at least one strain sensor is positioned neared to the tissue contacting surface than the fixed connection point.

10. The bipolar forceps tool as claimed in claim 1, further comprising an at least one further strain sensor mounted on each respective prong at a position proximal to the tip contacting position of the prongs and positioned in a plane perpendicular to both the plane on which each of the at least one strain sensor is mounted and the plane on which the at least one additional strain sensor is mounted, the at least one further strain sensor for measuring forces along a longitudinal axis of the prongs, perpendicular to both the compression and dissecting forces and upward and downward forces applied to the tips.

11. The bipolar forceps tool of claim 1 further comprising an at least one additional strain sensor mounted on each respective prong at a position thereon proximal to the tissue contacting surfaces of the tips of the prongs and positioned in a plane perpendicular to a plane on which the at least one strain sensor is mounted, the at least one additional strain sensor for measuring forces on its respective prong in a direction of the prong transverse to the prong and perpendicular to the direction of compression.

12. The bipolar forceps tool of claim 1 wherein said at least one strain sensor is arranged on said at least one prong to detect said bending movement of said at least a part of the respective prong.

13. The bipolar forceps tool of claim 12 wherein said at least one strain sensor is arranged on said at least one prong to measure compression forces in a direction of compression of the tips into the tip contacting position and to measure dissecting forces in a direction of spreading apart the tissue contacting surfaces of the tips.

14. The bipolar forceps tool of claim 1 wherein the at least one strain sensor is disposed on the surface of the at least one of the prongs.

15. The bipolar forceps tool of claim 1 wherein the fixed connection point is non-pivoting.

16. The bipolar forceps tool of claim 1 wherein each prong is disposed in an open position at rest and wherein each prong is adapted for movement to a closed or partially closed position in response to a force applied upon an outer surface of each prong.

* * * * *